US012582513B2

(12) United States Patent
     Flöss et al.

(10) Patent No.: US 12,582,513 B2
(45) Date of Patent: Mar. 24, 2026

(54) TOOL KIT FOR THE IMPLANTATION OF A TENDON FIXATION IMPLANT

(71) Applicant: INOVEDIS GMBH, Albstadt (DE)

(72) Inventors: Lukas Flöss, Inneringen (DE); Stefan Welte, Albstadt (DE)

(73) Assignee: INOVEDIS GmbH, Albstadt (DE)

( * ) Notice: Subject to any disclaimer, the term of this patent is extended or adjusted under 35 U.S.C. 154(b) by 0 days.

(21) Appl. No.: 18/876,708

(22) PCT Filed: Jun. 28, 2023

(86) PCT No.: PCT/EP2023/067706
     § 371 (c)(1),
     (2) Date: Dec. 19, 2024

(87) PCT Pub. No.: WO2024/003170
     PCT Pub. Date: Jan. 4, 2024

(65) Prior Publication Data
     US 2026/0000501 A1     Jan. 1, 2026

(30) Foreign Application Priority Data

Jul. 1, 2022     (DE) ........................ 102022116503.5

(51) Int. Cl.
     *A61F 2/08*          (2006.01)
(52) U.S. Cl.
     CPC .......... *A61F 2/0805* (2013.01); *A61F 2/0811*
     (2013.01); *A61F 2002/0835* (2013.01);
     (Continued)
(58) Field of Classification Search
     CPC ............ A61B 17/1146; A61B 17/1714; A61B
     17/7074; A61B 17/7076; A61B 17/7077;
     (Continued)

(56) References Cited

U.S. PATENT DOCUMENTS

| | | | | |
|---|---|---|---|---|
| 10,076,374 B2 * | 9/2018 | Diduch | ................. | A61B 17/88 |
| 2012/0130374 A1 * | 5/2012 | Bouduban | ............ | A61F 2/0805 |
| | | | | 606/75 |

FOREIGN PATENT DOCUMENTS

| | | |
|---|---|---|
| CA | 3186602 | 11/2021 |
| EP | 3020371 A2 | 5/2016 |

(Continued)

OTHER PUBLICATIONS

International Search Report and Written Opinion for PCT Application No. PCT/EP2023/067706, dated Oct. 17, 2023, 11 pages including English Translation.
(Continued)

*Primary Examiner* — Tan-Uyen T Ho
*Assistant Examiner* — Lindsay R. Rivers
(74) *Attorney, Agent, or Firm* — Christopher J. Volkmann; KELLY, HOLT & CHRISTENSON PLLC

(57)          ABSTRACT

A tool kit for minimally invasive implantation of a tendon fixation implant in the field of arthroscopic human medicine is provided. The tendon fixation implant includes a medial anchor, a lateral anchor, and a base plate. The tool kit includes a medial anchor inserter having a medial anchor drive mandrel and a medial anchor release tube. The medial anchor release tube is designed to receive the medial anchor drive mandrel. The medial anchor drive mandrel is designed both to receive a medial anchor and to introduce the medial anchor into bone by driving it into the latter. The medial anchor drive mandrel has a locking head for locking the medial anchor drive mandrel to the medial anchor release tube. The tool kit includes a base-plate inserter having a handpiece and a base-plate inserter tube designed to receive the base plate of the tendon fixation plate.

13 Claims, 3 Drawing Sheets

(52) U.S. Cl.
CPC ................. *A61F 2002/0841* (2013.01); *A61F 2002/0888* (2013.01); *A61F 2220/0016* (2013.01)

(58) Field of Classification Search
CPC .............. A61B 17/7079; A61B 17/708; A61B 17/7082; A61B 17/7083; A61B 17/7085; A61B 17/7086; A61B 17/7088; A61B 17/7089; A61B 17/7091; A61B 2017/0409; A61F 2/0805; A61F 2/0811; A61F 2002/0835; A61F 2002/0841; A61F 2002/0888; A61F 2220/0016
See application file for complete search history.

(56) References Cited

FOREIGN PATENT DOCUMENTS

| | | | |
|---|---|---|---|
| EP | 3020372 | A1 | 5/2016 |
| EP | 3184078 | A1 | 6/2017 |

OTHER PUBLICATIONS

International Preliminary Report on Patentability for International Application No. PCT/EP2023/067706, dated Oct. 9, 2024, 10 pages.

* cited by examiner

TOOL KIT FOR THE IMPLANTATION OF A TENDON FIXATION IMPLANT

CROSS-REFERENCES TO RELATED APPLICATIONS

This Application is a Section 371 National Stage Application of International Application No. PCT/EP2023/067706, filed Jun. 28, 2023, and published as WO 2024/003170 A1 on Jan. 4, 2024 and claims priority to German Application No. 102022116503.5, filed Jul. 1, 2022.

DETAILED DESCRIPTION

Figure 1:
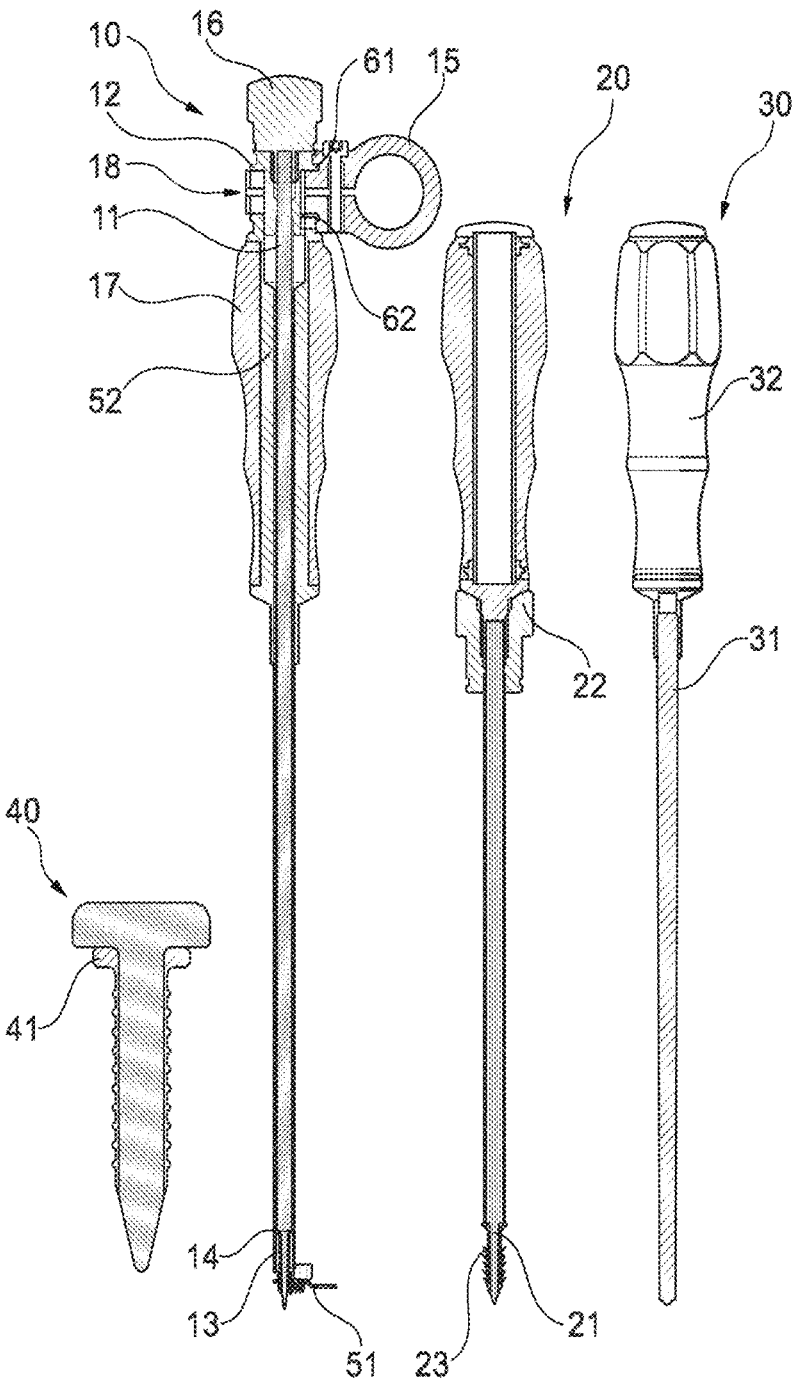
FIG. 1 shows a schematic view of a system comprising a tool kit together with a tendon fixation implant attached thereto, in one example.

The present disclosure relates to the technical field of tools for minimally invasive implantation of a tendon fixation implant in the field of arthroscopic human medicine, and to corresponding systems comprising a tendon fixation implant and a tool kit for minimally invasive implantation of the tendon fixation implant.

Various tools for introducing implants are already known. For example, the documents EP 3 020 371 A2 and EP 2 020 372 A1 disclose instruments that can be used for minimally invasive interventions in tendon operations. Tendon fixation implants are also known from, for example, CA 3 186 602 A1. The document EP 3 184 078 A1 discloses, in addition to an implant for planar connection of tissue to bone, a corresponding system for connecting tissue to bone, comprising at least one implant and at least one tool, wherein the tool comprises inter alia a gripping means and a shaft arranged rotationally conjointly thereon.

Proceeding from the prior art, it is a technical object of the present disclosure to afford a possibility of introducing tendon fixation implants in a manner that requires less effort and time.

In the context of the present disclosure, an anchor is to be understood as meaning a bone anchor, in particular a hollow anchor for bones.

Furthermore, in the context of one example of the present disclosure, an inserter is to be understood as meaning an arthroscopic insertion tool.

Furthermore, in the context of the one example of the present disclosure, an inlay is to be understood as meaning a holding device for receiving and releasing at least one anchor. The inlay is part of a package, the function of the inlay being to reliably protect the anchors and the base plate from damage during storage or transport. Furthermore, the inlay ensures simple removal of the tendon fixation implant. The anchors are held in position by means of an elastic deformation of a receptacle of the inlay, the base plate being held in position by a cap.

According to one aspect, a technical object of the present disclosure is achieved by means of a tool kit for minimally invasive implantation of a tendon fixation implant in the field of arthroscopic human medicine, wherein the tendon fixation implant comprises a medial anchor, a lateral anchor and a base plate, wherein the tool kit comprises a medial anchor inserter, wherein the medial anchor inserter comprises a medial anchor drive mandrel and a medial anchor release tube, wherein the medial anchor release tube is designed to receive the medial anchor drive mandrel, wherein the medial anchor drive mandrel is designed both to receive a medial anchor and to introduce the medial anchor into bone, wherein the medial anchor drive mandrel has a locking head for locking the medial anchor drive mandrel to the medial anchor release tube.

It is thus advantageously possible for at least parts of the tendon fixation implant to be introduced in a particularly time-efficient manner. The medial anchor can be received by means of the medial anchor drive mandrel, which can allow precise placement/rapid driving-in of the medial anchor onto/into the bone. In this case, the locking head offers a favorable possibility of fastening the anchor drive mandrel to the medial anchor release tube in a stable manner. It is thereby possible to significantly reduce the time required for performing a surgical intervention or introducing the tendon fixation implant.

The tool kit further comprises a base-plate inserter, a handpiece and a base-plate inserter tube, wherein the base-plate inserter tube is designed to receive the base plate of the tendon fixation plate and is designed to at least partially introduce the base plate into tissue or bone and designed to receive the medial anchor inserter within the handpiece and the base-plate inserter tube, wherein complete penetration of the medial anchor inserter into the base-plate inserter is temporarily prevented by means of a releasable stopper clip.

Advantageously, this can additionally promote particularly time-efficient introduction of at least parts of the tendon fixation implant. The base plate can be introduced in a stable and precise manner at the location of the implantation, and the parts of the tendon fixation implant can be fastened step by step by means of the stopper clip. Furthermore, this can have an advantageous effect on the accuracy of the surgical intervention.

In a further technically advantageous embodiment, provision is made that a respective collar is formed both on the medial anchor release tube and on the base-plate inserter.

Such collars advantageously afford the possibility, for example, of enabling interlocking engagement of any further elements which, on the one hand, can be used to enable a defined penetration depth of the base-plate inserter into the medial anchor release tube and, on the other hand, to prevent slipping out.

In an additionally technically advantageous embodiment, provision is made that the stopper clip is designed as a location-fixing bridge and/or, by means of the collars, is designed to interlockingly prevent an axial offset possible between the medial anchor release tube and the base-plate inserter.

In this way, it is advantageously possible to create a connection that can be closed or released quickly and easily, which can additionally have an advantageous effect of accelerating a surgical intervention.

In addition, in a technically advantageous embodiment, provision is made that the stopper clip is designed detachable, in particular able to be pulled off.

As a result, it is possible to do without complex holding mechanisms, and a simple configuration of the tool kit can thus be made possible.

In a further technically advantageous embodiment, provision is made that the stopper clip is designed, in particular slotted, in such a way that a first depth of penetration of the medial anchor into the bone is adjustable.

As a result, the introduction of the tendon fixation implant can be adapted flexibly and in a manner appropriate to any requirements.

In an additionally technically advantageous embodiment, the tool kit further comprises a lateral anchor inserter, wherein the lateral anchor inserter comprises a lateral anchor drive mandrel and a lateral anchor release tube, wherein the lateral anchor release tube is designed to receive the lateral anchor drive mandrel, wherein the lateral anchor drive mandrel is designed to receive a lateral anchor and to introduce the lateral anchor into bone.

Advantageously, this can additionally promote particularly time-efficient introduction of at least parts of the tendon fixation implant. The lateral anchor can be received by means of the medial anchor drive mandrel, which can allow precise placement/rapid driving-in of the lateral anchor onto/into the bone. As a result, it is additionally possible to significantly reduce the time required for performing a surgical intervention or introducing the tendon fixation implant.

Moreover, in a technically advantageous embodiment, provision is made that the medial anchor release tube is designed, at an end face of the medial anchor release tube, to bear on a support contour, in particular a collar surface, of the medial anchor.

Advantageously, a force which acts on the medial anchor, and which is to be applied for driving the latter into bone, can be distributed over a large area and uniformly onto an end face of the medial anchor, and any damage during introduction can be minimized. The medial anchor can thus be introduced into the bone in a simple and rapid manner, which can allow an additional time reduction.

Provision is furthermore made that the end face of the medial anchor release tube and the support contour, in particular the collar surface, of the medial anchor form a first push-off mechanism, which allows the medial anchor to be released from the medial anchor drive mandrel.

It is thus advantageously possible that the medial anchor, after being introduced into the bone, can be released quickly and reliably from the medial anchor drive mandrel and in the meantime can be held fixed in its position in the bone.

Provision is furthermore made that the lateral anchor release tube is designed, at an end face of the lateral anchor release tube, to bear on a support contour, in particular a collar surface, of the lateral anchor.

Advantageously, a force which acts on the lateral anchor, and which is to be applied for driving the latter into bone, can be distributed over a large area and uniformly onto an end face of the lateral anchor, and possible damage during introduction can be minimized. The lateral anchor can thus be introduced into the bone in a simple and rapid manner, which can allow an additional time reduction.

Provision is furthermore made that the end face of the lateral anchor release tube (22) and the support contour, in particular the collar surface, of the lateral anchor (23) form a second push-off mechanism, which allows the lateral anchor (23) to be released from the lateral anchor drive mandrel (21).

It is thus advantageously possible that the lateral anchor, after being introduced into the bone, can be released quickly and reliably from the lateral anchor drive mandrel and in the meantime can be held fixed in its position in the bone.

Furthermore, in a technically advantageous embodiment, the tool kit further comprises a re-impact tool comprising a re-impact drive mandrel and a re-impact handpiece.

This can advantageously permit further driving-in of the anchors of the tendon fixation implant.

Furthermore, in a technically advantageous embodiment, the tool kit further comprises a trocar.

This advantageously affords the surgeon the possibility of opening a wound canal during the surgical introduction of the tendon fixation implant and of keeping it open during the intervention.

In an additionally technically advantageous embodiment, the tool kit furthermore comprises an inlay, wherein the inlay is designed to receive the tendon fixation plate, the medial anchor and the lateral anchor, wherein the inlay has a marking for clearly distinguishing the anchors.

This can have an advantageous effect on rapid performance of the surgical intervention, since a distinction can be made quickly between the medial anchor and the lateral anchor, and the correct anchor can be selected for the respective part of the intervention. Moreover, it is thus possible for at least individual elements of the tendon fixation implant to be transported safely and in a manner protected from damage or contamination.

It is furthermore provided that introduction of the medial anchor and/or of the lateral anchor into the bone is made possible without a bore, in particular without a pilot bore.

Advantageously, additional work steps can thus be avoided and an additional time reduction can be made possible.

According to a further aspect, a technical object of the present disclosure is achieved by means of a system comprising a tendon fixation implant and a tool kit for minimally invasive implantation of the tendon fixation implant, wherein the tendon fixation implant comprises a medial anchor, a lateral anchor and a base plate.

In this way, an accelerated and rapid surgical intervention for fixing tissue to bone can additionally be advantageously made possible.

Exemplary embodiments of the present disclosure are illustrated in the drawings and are described in more detail below.

All of the features explained in conjunction with individual embodiments of the present disclosure may be provided in various combinations in the subject matter according to the present disclosure in order to simultaneously realize the advantageous effects thereof.

The scope of protection of the present disclosure is specified by the claims and is not restricted by the features explained in the description or shown in the figures.

FIG. 1 shows a schematic view of a system comprising a tool kit for minimally invasive implantation of a tendon fixation implant, which is shown situated on the tool kit.

Here, the tendon fixation implant illustrated comprises a medial anchor 13 with a medial anchor head 14, a base plate 51, and a lateral anchor 23.

The tool kit illustrated comprises a trocar 40 with a trocar tube 41, a re-impact tool 30 with a re-impact drive mandrel 31 and a re-impact handpiece 32, a lateral anchor inserter 20 with a lateral anchor drive mandrel 21 and a lateral anchor release tube 22. Furthermore, the tool kit illustrated comprises a medial anchor inserter 10 with medial anchor inserter handpiece 17, medial anchor drive mandrel 11, medial anchor release tube 12, locking head 16, and stopper clip 15 with slot 18.

Furthermore, a collar of the release tube 61 and the collar of the base-plate inserter 62 are illustrated. The stopper clip 15 is designed as a location-fixing bridge and, in cooperation with the collars 61, 61, interlockingly prevents an axial offset that is possible between the medial anchor release tube 12 and the base-plate inserter 52.

For example, it is thus possible to prevent an excessively deep penetration of the medial anchor into a bone (not shown).

In the interaction between the individual elements of the medial anchor inserter, the medial anchor can initially be introduced partially into a bone (not shown in FIG. 1) by a force action introduced onto the locking head 16, and on account of the slot 18 of the stopper clip 15, and then, as a result of removal of the stopper clip 15, can be introduced further into said bone. In addition, it is conceivable that a slot width of the slot 18 can be adjustable by means of a mechanism (not defined in any more detail), for example an adjusting screw, in order to allow greater flexibility in a surgical intervention.

The stopper clip 15 is designed to be releasable and detachable and can be pulled off in a time-efficient and simple manner in the radial direction with respect to the anchor inserter 10, thus enabling a surgeon to work quickly. The lateral anchor 23 can then likewise be quickly introduced into the bone by means of the lateral anchor inserter 20.

Figure 2:
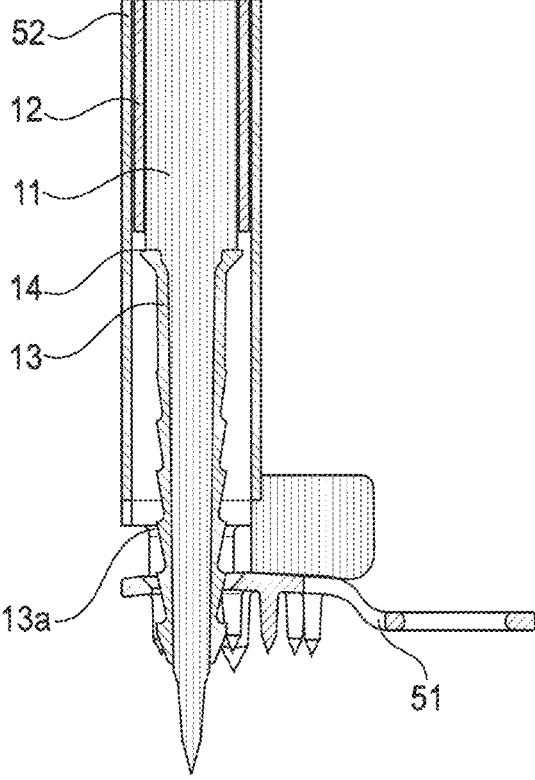
FIG. 2 shows a schematic detail view of the tip of the medial anchor inserter, in one example.

FIG. 2 shows a schematic detail view of the tip of the medial anchor inserter 10 shown in FIG. 1. The medial anchor 13 is held plugged onto the medial anchor drive mandrel 12, the latter being shown inserted into the medial anchor release tube 12. For its part, the medial anchor release tube 12 is shown inserted into the base-plate inserter 52, wherein a base plate 51 is located on said inserter. The base plate 51 has an opening, not defined in any more detail, through which the lateral anchor 23 shown in FIG. 1 or in FIG. 3 can be quickly introduced by means of the lateral anchor inserter 20.

Figure 3:
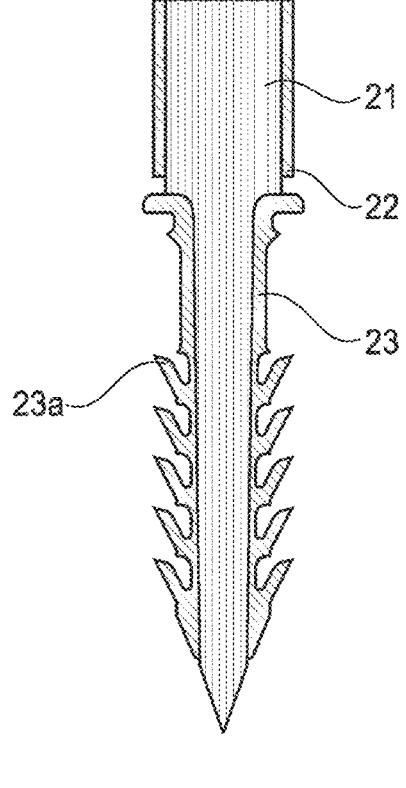
FIG. 3 shows a schematic detail view of the tip of the lateral anchor inserter, in one example.

It is also shown that the medial anchor release tube 12 is designed, at an end face (not defined in any more detail), to bear on a support contour, for example a collar surface of the medial anchor 13. This is shown analogously in FIG. 3 for the lateral anchor release tube and the lateral anchor. In FIG. 3, the lateral anchor release tube is designed, at an end face (likewise not defined in any more detail), to bear on a support contour, for example a collar surface of the lateral anchor 14.

It can additionally be seen from comparison of FIG. 1 and FIG. 2 that the stopper clip 15 temporarily prevents the complete penetration of the medial anchor 13 into the base plate 51, in the sense that the head 14 of the medial anchor rests on the base plate 51.

Furthermore, the medial anchor 13 has blocking elements in the form of barbs 13a.

In a further embodiment, the medial anchor 13 can also (analogously) have blocking elements, corresponding to the lateral anchor 23, with further projecting barbs or pawls 23a. Preferably, these pawls 23a can also be (analogously) formed circumferentially, offset by 90° in sections, or alternately as barbs and pawls with in each case an axis of symmetry rotated through 90° with respect to one another.

FIG. 3 shows a schematic detail view of the tip of the lateral anchor inserter 20 shown in FIG. 1. The lateral anchor 23 is held plugged onto the lateral anchor drive mandrel, the latter being situated within the lateral anchor release tube 22.

Furthermore, the lateral anchor 23 has blocking elements in the form of pawls 23a.

Figure 4:
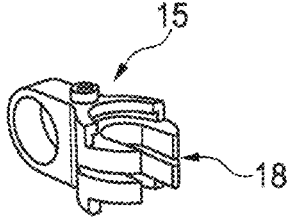
FIG. 4 shows a schematic view of a stopper clip, in one example.

FIG. 4 shows a schematic view of a stopper clip 15 with slot 18. A comparison of FIG. 4 with FIG. 1 shows how the stopper clip 15, in cooperation with the collar of the release tube 61 and with the collar of the base-plate inserter, releasably prevents the medial anchor from penetrating too far or too little.

All of the features explained in conjunction with individual embodiments of the invention may be provided in various combinations in the subject matter according to the invention in order to simultaneously realize the advantageous effects thereof.

The scope of protection of the present invention is specified by the claims and is not restricted by the features explained in the description or shown in the figures.

Although the present invention has been described with reference to preferred embodiments, workers skilled in the art will recognize that changes may be made in form and detail without departing from the spirit and scope of the invention.

LIST OF REFERENCE SIGNS 10 medial anchor inserter
11 medial anchor drive mandrel
12 medial anchor release tube
13 medial anchor
13a barbs
14 head of the medial anchor
15 stopper clip
16 locking head
17 handpiece of the medial anchor inserter
18 slot
20 lateral anchor inserter
21 lateral anchor drive mandrel
22 lateral anchor release tube
23 lateral anchor
23a pawls
30 re-impact tool
31 re-impact drive mandrel
32 re-impact handpiece
40 trocar
41 trocar tube
51 base plate
52 base-plate inserter
52 base-plate inserter tube
53 barbs/tabs
54 marking
61 collar of the release tube
62 collar of the base-plate inserter

The invention claimed is:
1. A tool kit for minimally invasive implantation of a tendon fixation implant, wherein the tendon fixation implant comprises a medial anchor, a lateral anchor and a base plate, wherein
the tool kit comprises a medial anchor inserter,
wherein the medial anchor inserter comprises a medial anchor drive mandrel and a medial anchor release tube,
wherein the medial anchor release tube is configured to receive the medial anchor drive mandrel,
wherein the medial anchor drive mandrel is configured to receive the medial anchor and to introduce the medial anchor into bone by driving the medial anchor into the bone,
wherein the medial anchor drive mandrel has a locking head for locking the medial anchor drive mandrel to the medial anchor release tube,
wherein the tool kit comprises a base-plate inserter, which base-plate inserter comprises a handpiece and a base-plate inserter tube, wherein the base-plate inserter tube is configured to receive the base plate of the tendon fixation implant and is configured to at least partially introduce the base plate into tissue or bone and configured to receive the medial anchor inserter within the handpiece and the base-plate inserter tube, wherein complete penetration of the medial anchor insert into the base-plate inserter is temporarily prevented by a releasable stopper clip.

2. The tool kit as claimed in claim 1, wherein a respective collar is formed both on the medial anchor release tube and on the base-plate inserter.

3. The tool kit as claimed in claim 1, wherein the releasable stopper clip is a location-fixing bridge and/or, is configured to interlockingly prevent an axial offset between the medial anchor release tube and the base-plate inserter.

4. The tool kit as claimed in claim 1, wherein the releasable stopper clip is configured to be releasable.

5. The tool kit as claimed in claim 1, wherein the releasable stopper clip is slotted and configured such that a first depth of penetration of the medial anchor into the bone is adjustable.

6. The tool kit as claimed in claim 1, further comprising a lateral anchor inserter, wherein the lateral anchor inserter comprises a lateral anchor drive mandrel and a lateral anchor release tube, wherein the lateral anchor release tube is configured to receive the lateral anchor drive mandrel, wherein the lateral anchor drive mandrel is configured to receive the lateral anchor and to introduce the lateral anchor into bone.

7. The tool kit as claimed in claim 1, wherein the medial anchor release tube is configured, at an end face of the medial anchor release tube, to bear on a support contour of a medial anchor.

8. The tool kit as claimed in claim 7, wherein the end face of the medial anchor release tube and the support contour of the medial anchor form a first push-off mechanism, which allows the medial anchor to be released from the medial anchor drive mandrel.

9. The tool kit as claimed in claim 6, wherein the lateral anchor release tube is configured, at an end face of the lateral anchor release tube, to bear on a support contour of the lateral anchor.

10. The tool kit as claimed in claim 9, wherein the end face of the lateral anchor release tube and with the support contour of the lateral anchor form a second push-off mechanism, which allows the lateral anchor to be released from the lateral anchor drive mandrel.

11. The tool kit as claimed in claim 1, further comprising a re-impact tool, which comprises a re-impact drive mandrel and a re-impact handpiece.

12. The tool kit as claimed in claim 1, further comprising a trocar.

13. A system comprising a tendon fixation implant, wherein the tendon fixation implant and a tool kit for minimally invasive implantation of the tendon fixation implant, wherein the tendon fixation implant comprises: a medial anchor, a lateral anchor, and a base plate, and a tool kit for minimally invasive implantation of the tendon fixation implant,
    wherein the tool kit comprises a medial anchor inserter,
    wherein the medial anchor inserter comprises a medial anchor drive mandrel and a medial anchor release tube,
    wherein the medial anchor release tube is configured to receive the medial anchor drive mandrel,
    wherein the medial anchor drive mandrel is configured to receive the medial anchor and to introduce the medial anchor into bone by driving the medial anchor into the bone,
    wherein the medial anchor drive mandrel has a locking head for locking the medial anchor drive mandrel to the medial anchor release tube,
    wherein the tool kit comprises a base-plate inserter, which base-plate inserter comprises a handpiece and a base-plate inserter tube,
    wherein the base-plate inserter tube is configured to receive the base plate of the tendon fixation implant and is configured to at least partially introduce the base plate into tissue or bone and configured to receive the medial anchor inserter within the handpiece and the base-plate inserter tube,
    wherein complete penetration of the medial anchor insert into the base-plate inserter is temporarily prevented by a releasable stopper clip.

* * * * *